United States Patent
Zhang et al.

(10) Patent No.: US 9,861,722 B2
(45) Date of Patent: Jan. 9, 2018

(54) METHOD FOR PREPARING OXIDIZED CELLULOSE HEMOSTATIC PRODUCT

(71) Applicants: Hangzhou Singclean Medical Products Co., Ltd, Hangzhou, Zhejiang (CN); Zhejiang University of Science and Technology, Hangzhou, Zhejiang (CN)

(72) Inventors: Zhiguo Zhang, Zhejiang (CN); Yange Suo, Zhejiang (CN); Wei Huang, Zhejiang (CN); Weiqing Sun, Zhejiang (CN)

(73) Assignees: Hangzhou Singclean Medical Products Co., Ltd, Hangzhou (CN); Zhejiang University of Science and Technology, Hangzhou (CN)

( * ) Notice: Subject to any disclaimer, the term of this patent is extended or adjusted under 35 U.S.C. 154(b) by 0 days.

(21) Appl. No.: 15/201,597

(22) Filed: Jul. 4, 2016

(65) Prior Publication Data
US 2017/0182203 A1    Jun. 29, 2017

(30) Foreign Application Priority Data

Dec. 28, 2015  (CN) .......................... 2015 1 1000604

(51) Int. Cl.
*A61L 24/00* (2006.01)
*A61L 24/08* (2006.01)
*C08B 15/04* (2006.01)

(52) U.S. Cl.
CPC ........... *A61L 24/0036* (2013.01); *A61L 24/08* (2013.01); *C08B 15/04* (2013.01); *A61L 2400/04* (2013.01)

(58) Field of Classification Search
None
See application file for complete search history.

(56) References Cited

U.S. PATENT DOCUMENTS

2007/0054880 A1*   3/2007  Saferstein ............... A61L 15/28
                                                            514/57

\* cited by examiner

*Primary Examiner* — Aradhana Sasan

(57) ABSTRACT

Disclosed is a method for preparing an oxidized cellulose hemostatic product, including using a sodium hydroxide solution with the concentration of 1 to 5% to pre-process a cellulose product; after removing lignins or impurities on the fiber surface, using an alkaline solution to activate the fiber surface further; after the activating treatment, using deminwater for washing until it is neutral and drying the obtained cellulose product in air to obtain a raw material; using a sodium hydroxide solution with the concentration of 5 to 20% as a solvent; adding the cellulose product, carbamide and ZnO that are 3 to 10%, 2% and 2% of the sodium hydroxide solution respectively.

10 Claims, No Drawings

METHOD FOR PREPARING OXIDIZED CELLULOSE HEMOSTATIC PRODUCT

CROSS-REFERENCE TO RELATED APPLICATION

This application claims priority from Chinese Patent Application No. 201511000604.7, filed on Dec. 28, 2015, which is incorporated by reference in its entirety.

FIELD OF THE INVENTION

The invention relates to the field of cellulose hemostatic products, in particular to a method for preparing a new oxidized cellulose hemostatic product (hemostatic sponge).

BACKGROUND

Cellulose is the macromolecular polysaccharide formed by glucose, which is insoluble in general organic solvents or water. As the chief constituent of plant cell walls, cellulose is the most widely distributed and abundant polysaccharide in nature, accounting for more than 50% of the carbon content in the plant kingdom, where the cotton is the purest source of cellulose with the content thereof of nearly 100%. Cellulose is a natural polymeric compound formed by the attachment of D-glucopyranose.

With characteristics of sound biocompatibility and degradability, the oxidized cellulose and oxidized regenerated cellulose can be used in medical field as hemostatic gauze products. After being made into the medical gauze, the carboxyl group of the oxidized cellulose can cross-link with the calcium ions of plasma, resulting in the reaction of the oxidized cellulose and hemoglobin, which forms artificial blood clots, thereby realizing the function of hemostasis. In addition, over other hemostatic means for wounds, it has advantages of being able to degrade gradually and to be absorbed and degraded by human body, and having biocompatibility and absorbability so that it is easy to use without the necessity of being taken out. Currently, the medical absorbable hemostatic gauze called Surgical produced by Johnson & Johnson is the most widely used for clinical applications. With comparatively larger specific surface area, high cost and slower hemostatic speed, Surgical needs 2 to 8 minutes to stop bleeding, and is suitable for the wound with lower blood loss. But for the parts with severe blood loss, Surgical is not applicable because it is unable to absorb rapidly, timely and effectively. In addition, the existing form of the product is adverse to the combination with other products and new alternative products are in urgent need of development.

Currently, the oxidization reactions of cellulose can be divided into selective and non-selective oxidations. In the prior art, it is hoped that the oxidized cellulose is selectively oxidized, which can be divided into selective oxidations of secondary hydroxyl at positions of C2 and C3, and that of primary hydroxyl at position of C6. The oxidation systems of this sort mainly include nitrogen dioxide oxidation system and other oxidation systems of nitrogen oxides. Nevertheless, some key problems in the oxidization reactions of the cellulose by using the selective oxidation technology in the prior art remain to be solved. All the current products of the oxidized cellulose hemostatic gauze have problems, such as low intensity of gauze, insufficient storage stability, nonuniform carboxyl content, low absorptivity and uncontrollability of degradation time and the like, which restricts the application and promotion of such products.

In addition, existing oxidized cellulose and oxidized regenerated cellulose products all adopt cellulose fabrics as raw materials, which are subject to the oxidation reaction, washing and post-processing further, thereby obtaining the hemostatic gauze products. Products of this sort share similar problems with Surgical. With comparatively larger specific surface area, high cost and slower hemostatic speed, products of this sort need 2 to 8 minutes to stop bleeding, and are suitable for the wound with lower blood loss but for the parts with severe blood loss which they are unable to absorb rapidly, timely and effectively. In addition, the existing forms of these products are adverse to the combinations with other products and new alternative products are in urgent need of development. As ordinary cellulose fabrics have defects of small absorptive amount, low porosity of products (those of ordinary gauzes and Surgical are usually less than 70%) and limited fabric weight, these problems cannot be solved well. To sum up, various existing methods and products have different defects, and are in urgent need of improvement.

Generally the sponge has the advantages of sound filling power, soft texture and good water absorptivity, thereby being widely applied. However, the sponge generally consists of substances such as polystyrene and polyurethane which are harmful to human body and the environment. The cellulose sponge is a porous cellulose product prepared with the cellulose as the basic material through a certain method to replace the traditional sponge, characterized by easiness to dry, durability and high liquid absorptivity and the like. Cellulose is biodegradable polymer so that the cellulose sponge is of great significance.

SUMMARY

To eliminate various defects in the prior art, the present invention provides a method for preparing an oxidized cellulose hemostatic product (hemostatic sponge).

For this purpose, the invention is achieved by using the following technical solutions:

The invention discloses a method for preparing oxidized cellulose hemostatic products, including the following steps:

1). Using a sodium hydroxide solution with the concentration of 1 to 5% to pre-process a cellulose product, and after removing lignins or impurities on the fiber surface, using an alkaline solution to activate the fiber surface further;

2). After the activating treatment, using demin-water for washing until neutral and drying the obtained cellulose products in air to obtain a raw material;

3). Using a sodium hydroxide solution with the concentration of 5 to 20% as a solvent, adding the cellulose product, carbamide and ZnO that are 3 to 10%, 2% and 2% of the sodium hydroxide solution respectively, and intensively dissolving them under the temperature of −15 to 5° C. to obtain a viscose system;

4). After the fibers thoroughly dissolve in the solution with a viscose form, adding slowly sodium sulfate as a pore-forming agent and stirring continuously for 20 minutes to make it into a cellulose mixture;

5). Pouring the cellulose mixture into a mould to gelate; during standing, the cellulose solution becoming gelatin due to the increasing of the viscosity and the loss of mobility, and aging the product for 3 to 24 hours under the condition of −20° C. and −12° C.;

6). After forming the cellulose gelatin, immersing cellulose gelatin firstly in a coagulating bath under 50 to 70° C., retexturing it for 1 to 3 hours, using demin-water finally for washing until it is neutral, and discharging the wash water to obtain a raw material of the cellulose sponge product;

7). Adding an anhydrous ethanol solvent until the raw material of the cellulose sponge product is completely immersed, and after repeated washing, discharging the liquid;

8). Performing vacuum drying, and obtaining the preprocessed material of the cellulose sponge after fully drying;

9). Adding anhydrous cyclohexane or methyl cyclohexane into an oxidation reactor, adding the preprocessed material of the cellulose sponge, strictly controlling the water content of the system to be less than 0.3%, ensuring that the material of the cellulose sponge is completely immersed in the solution, opening the vacuum to empty the remaining air in the system, and reserving for further use;

10). Introducing $NO_2$ gas into the reaction system, and making the concentration of the $NO_2$ gas to be 0.2-4.0 mol/L in the oxidation reaction system; sealing the reaction system and the oxidation reaction of the cellulose sponge material starting at room temperature;

11). After 10-to-40-hour reaction, discharging the oxidation reaction solution into a storage tank;

12). After the reaction, adding the cyclohexane or methyl cyclohexane firstly for washing, and after sonicating for 5 minutes, discharging the liquid; using an ethanol water solution with the mass percent of 50 to 95% for immersion and washing, and after sonicating for 5 minutes, discharging the liquid; when the pH of the effluent is equal to 5 to 7 after repeated washing, using anhydrous ethanol for immersion and washing again, and after sonicating for 5 minutes, discharging the liquid; and 13). Introducing dry $N_2$ gas to dry the obtained oxidized regenerated cellulose;

As a further improvement, according to the invention, the cellulose product is cotton fibers, wood fibers or viscoses with the fiber fineness of 0.5 to 3.0 deniers.

As a further improvement, according to the invention, the coagulating bath contains sodium sulfate and sulfuric acid both with the concentration of 3 to 5% in the step 6).

As a further improvement, according to the invention, air drying for products at room temperature is adopted to replace vacuum drying in the step 8).

As a further improvement, according to the invention, vacuum freeze drying is adopted to replace drying with $N_2$ gas in the step 13).

As a further improvement, according to the invention, the carboxyl content of the prepared oxidized cellulose hemostatic product is between 15 and 24% and the porosity thereof is more than 90%.

The invention has following advantages:

1. The cellulose sponge product is prepared firstly with cellulose. The cellulose fibers are reasonably pre-processed to remove the surface impurities and activate the fiber surface, and then the sodium hydroxide solution is used as the solvent and carbamide and ZnO are added to accelerate the dissolution of the cellulose fibers, thereby obtain the viscous solution. The sodium sulfate as the pore-forming agent is added for the treatment of gelation. Finally, through washing in the coagulating bath, raw material of the cellulose sponge is obtained, which is characterized by soft texture, high porosity, strong liquid absorptivity, durability and easiness to dry.

This directly changes the physical properties of the cellulose fibers with greatly increased porosity, expanded specific surface area, strengthened intensity of the cellulose products and improved crystallization morphology and structure of the cellulose, which are significantly beneficial to the next selective oxidation reaction.

2. The reaction processes are strictly controlled in the oxidation reaction system. The water content of the raw material of the cellulose sponge is strictly controlled. After immersion and washing, the raw material of the cellulose sponge is dewatered by the anhydrous ethanol solvent through displacement to the greatest extent and then completely dried to ensure that the system has no water. The water content of the organic solvent is further controlled in the reaction system to stringently ensure that the water content in the reaction system is less than 0.3%. When the material of the cellulose sponge is immersed, the vacuum is opened to empty the remaining air thereof. Through these processes, the oxidation reaction is under strict control. As the system has no water and free oxygen, non-selective oxidation side reactions in the system are reduced greatly, thereby improving the performance of the product.

3. During the oxidation reaction, all the reported reaction systems are substantially under the state of standing reaction and short of sufficient mass-transfer power, causing longer reaction time, acuter degradation of the oxidized cellulose and difficulty of steadily controlling the degree of the oxidation. In the present application, the physical properties of the cellulose fibers of the prepared material of the cellulose sponge are directly changed with greatly increased porosity, expanded specific surface area, strengthened intensity of the cellulose products and improved crystallization morphology and structure of the cellulose. All these changes of properties are beneficial to the selective oxidation reaction of the products. The reaction time is greatly shortened and the expanded specific surface area is also in favor of the uniformity of the oxidation reaction, thereby making the degradation time of the final products and the solubility property under control and uniforming the degree of oxidation and the carboxyl content.

Furthermore, in conventional preparations of the oxidized cellulose, the stationary state of the reaction leads to long reaction time. However, long oxidation reaction will cause constant oxidation reaction of the reaction solvent, producing carboxylic acid substances that stick to the cellulose fabrics, which further results in quick degradation of the macromolecular chains of the cellulose as well as nonuniform distribution of the carbonyl content during the oxidation. These problems cause the performance reduction, the insufficient storage stability and the low absorptivity of the oxidized products. In the present application, the reaction time is shortened so that various side reactions are greatly reduced and the rapid degradation of the macromolecular chains of cellulose is suppressed.

4. The post-processing means for products are optimized. At present, it is reported in literature that after preparation by oxidation, various oxidized cellulose products are obtained only by washing for deacidification and drying treatment afterwards. However, in some reports, washing with deminwater and vacuum drying under 80° C. are adopted. According to some reports, after washing with alcohols, air drying is adopted to obtain products. Our experiments show that all these post-processing means will greatly lower the storage stability of the oxidized fiber products. As the oxidized cellulose has higher carbonyl content, its molecules are under highly active state. Therefore, conventional post-processing means are adverse to the storage stability of the products.

In the present application, after the oxidation reaction, cyclohexane or methyl cyclohexane is added firstly for ultrasonic washing, then ethanol water with the mass percent of 50 to 95% is used for immersion and sonicating, and finally anhydrous ethanol is used for immersion and sonicating to obtain the pure oxidized cellulose hemostatic product (hemostatic sponge). At this time, the molecules of the oxidized cellulose are under highly active state, unsuitable to be directly dried or rapidly placed in air. In the present application, dry $N_2$ gas is introduced into the reaction equipment to dry the obtained oxidized regenerated cellulose. Alternatively, the process of freeze drying can be adopted as well. Both technologies can ensure the stability of the products. The completely dried products are the absorbable oxidized cellulose hemostatic product with high porosity and absorptive amount.

DETAILED DESCRIPTION OF THE INVENTION

The technical solutions of the invention will be further described in detail with reference to the embodiments below.

Embodiment 1

The wood fibers are used as the raw material, and the fiber fineness of the raw material is 0.5 denier.

1. Use a sodium hydroxide solution with the concentration of 1% to pre-process a cellulose product, and after removing possible impurities, use an alkaline solution to activate the fiber surface further;
2. After the activating treatment, use demin-water for washing until neutral and dry the obtained cellulose products in air to obtain a raw material;
3. Use a sodium hydroxide solution with the concentration of 5% as a solvent, add the cellulose product, carbamide and ZnO that are 3%, 2% and 2% of the sodium hydroxide solution respectively, and intensively dissolve them under the temperature of −15° C. to obtain a viscose system;
4. After the fibers thoroughly dissolve in the solution with a viscose form, add slowly sodium sulfate as a pore-forming agent and stir continuously for 20 minutes to make it into a cellulose mixture;
5. Pour the cellulose mixture into a mould to gelate; during standing, the cellulose solution becomes gelatin due to the increasing of the viscosity and the loss of mobility, and age the product for 3 hours under the condition of −20° C.;
6. After forming the cellulose gelatin, immerse cellulose gelatin firstly in a coagulating bath under 50° C., where the coagulating bath contains the sodium sulfate and the sulfuric acid both with the concentration of 3%; retexture it for 1 hour, use demin-water finally for washing until it is neutral, and discharge the wash water to obtain a raw material of the cellulose sponge product;
7. Add an anhydrous ethanol solvent until the raw material of the cellulose sponge product is completely immersed, and after repeated washing, discharge the liquid;
8. Perform vacuum drying, or dry the product at room temperature, and obtain the preprocessed material of the cellulose sponge after fully drying;
9. Add anhydrous cyclohexane into an oxidation reactor, add the preprocessed material of the cellulose sponge, strictly control the water content of the system to be less than 0.3%, ensure that the material of the cellulose sponge is completely immersed in the solution, open the vacuum to empty the remaining air in the system, and reserve for further use;
10. Introduce $NO_2$ gas into the reaction system, and make the concentration of the $NO_2$ gas to be 0.2 mol/L in the oxidation reaction system; seal the reaction system, and the oxidation reaction of the cellulose sponge material starts at room temperature;
11. After 40-hour reaction, discharge the oxidation reaction solution into a storage tank;
12. After the reaction, add the cyclohexane or methyl cyclohexane firstly for washing, and after sonicating for 5 minutes, discharge the liquid; use an ethanol water solution with the mass percent of 50% for immersion and washing, and after sonicating for 5 minutes, discharge the liquid; when the pH of the effluent is equal to 5 after repeated washing, use anhydrous ethanol for immersion and washing again, and after sonicating for 5 minutes, discharge the liquid;
13. Introduce dry $N_2$ gas to dry the obtained product, that is, the obtained oxidized cellulose sponge material; and
14. Obtain the completely dried products, that is, the absorbable oxidized cellulose hemostatic product with high porosity and absorptive amount.

The carbonyl content of the prepared oxidized cellulose hemostatic product (hemostatic sponge) is 20% and the porosity thereof is more than 90%.

Embodiment 2

The viscoses are used as the raw material, and the fiber fineness of the raw material is 1.0 denier.

1. Use a sodium hydroxide solution with the concentration of 3% to pre-process a cellulose product, and after remove impurities on the fiber surface, use an alkaline solution to activate the fiber surface further;
2. After the activating treatment, use demin-water for washing until neutral and dry the obtained cellulose products in air to obtain a raw material;
3. Use a sodium hydroxide solution with the concentration of 10% as a solvent, add the cellulose product, carbamide and ZnO that are 5%, 2% and 2% of the sodium hydroxide solution respectively, and intensively dissolve them under the temperature of −5° C. to obtain a viscose system;
4. After the fibers thoroughly dissolve in the solution with a viscose form, add slowly sodium sulfate as a pore-forming agent and stir continuously for 20 minutes to make it into a cellulose mixture;
5. Pour the cellulose mixture into a mould to gelate; during standing, the cellulose solution becomes gelatin due to the increasing of the viscosity and the loss of mobility, and age the product for 12 hours under the condition of −18° C.;
6. After forming the cellulose gelatin, immerse cellulose gelatin firstly in a coagulating bath under 60° C., where the coagulating bath contains the sodium sulfate and the sulfuric acid both with the concentration of 4%; retexture it for 2 hours, use demin-water finally for washing until it is neutral, and discharge the wash water to obtain a raw material of the cellulose sponge product;
7. Add an anhydrous ethanol solvent until the raw material of the cellulose sponge product is completely immersed, and after repeated washing, discharge the liquid;
8. Perform vacuum drying, or dry the product at room temperature, and obtain the preprocessed material of the cellulose sponge after fully drying;
9. Add anhydrous methyl cyclohexane into an oxidation reactor, add the preprocessed material of the cellulose sponge, strictly control the water content of the system to be less than 0.3%, ensure that the material of the cellulose sponge is completely immersed in the solution, open the vacuum to empty the remaining air in the system, and reserve for further use;

10. Introduce $NO_2$ gas into the reaction system, and make the concentration of the $NO_2$ gas to be 2.0 mol/L in the oxidation reaction system; seal the reaction system, and the oxidation reaction of the cellulose sponge material starts at room temperature;

11. After 20-hour reaction, discharge the oxidation reaction solution into a storage tank;

12. After the reaction, add the methyl cyclohexane firstly for washing, and after sonicating for 5 minutes, discharge the liquid; use an ethanol water solution with the mass percent of 75% for immersion and washing, and after sonicating for 5 minutes, discharge the liquid; when the pH of the effluent is equal to 6 after repeated washing, use anhydrous ethanol for immersion and washing again, and after sonicating for 5 minutes, discharge the liquid;

13. Introduce dry $N_2$ gas to dry the obtained product, and perform vacuum freeze drying on the obtained oxidized cellulose material; and 14. Obtain the completely dried products, that is, the absorbable oxidized cellulose hemostatic product with high porosity and absorptive amount.

The carbonyl content of the prepared oxidized cellulose hemostatic products (hemostatic sponges) is 24% and the porosity thereof is more than 90%.

Embodiment 3

The cotton fibers are used as the raw material, and the fiber fineness of the raw material is 3.0 deniers.

1. Use a sodium hydroxide solution with the concentration of 5% to pre-process a cellulose product, and after removing impurities on the fiber surface, use an alkaline solution to activate the fiber surface further;

2. After the activating treatment, use demin-water for washing until neutral and dry the obtained cellulose products in air to obtain a raw material;

3. Use a sodium hydroxide solution with the concentration of 20% as a solvent, add the cellulose product, carbamide and ZnO that are 10%, 2% and 2% of the sodium hydroxide solution respectively, and intensively dissolve them under the temperature of 5° C. to obtain a viscose system;

4. After the fibers thoroughly dissolve in the solution with a viscose form, add slowly sodium sulfate as a pore-forming agent and stir continuously for 20 minutes to make it into a cellulose mixture;

5. Pour the cellulose mixture into a mould to gelate; during standing, the cellulose solution becomes gelatin due to the increasing of the viscosity and the loss of mobility, and age the product for 24 hours under the condition of −12° C.;

6. After forming the cellulose gelatin, immerse cellulose gelatin firstly in a coagulating bath under 70° C., where the coagulating bath contains the sodium sulfate and the sulfuric acid both with the concentration of 5%; retexture it for 3 hours, use demin-water finally for washing until it is neutral, and discharge the wash water to obtain a raw material of the cellulose sponge product;

7. Add an anhydrous ethanol solvent until the raw material of the cellulose sponge product is completely immersed, and after repeated washing, discharge the liquid;

8. Perform vacuum drying, or dry the product at room temperature, and obtain the preprocessed material of the cellulose sponge after fully drying;

9. Add anhydrous cyclohexane into an oxidation reactor, add the preprocessed material of the cellulose sponge, strictly control the water content of the system to be less than 0.3%, ensure that the material of the cellulose sponge is completely immersed in the solution, open the vacuum to empty the remaining air in the system, and reserve for further use;

10. Introduce $NO_2$ gas into the reaction system, and make the concentration of the $NO_2$ gas to be 4.0 mol/L in the oxidation reaction system; seal the reaction system, and the oxidation reaction of the cellulose sponge material starts at room temperature;

11. After 10-hour reaction, discharge the oxidation reaction solution into a storage tank;

12. After the reaction, add the cyclohexane or methyl cyclohexane firstly for washing, and after sonicating for 5 minutes, discharge the liquid; use an ethanol water solution with the mass percent of 95% for immersion and washing, and after sonicating for 5 minutes, discharge the liquid; when the pH of the effluent is equal to 7 after repeated washing, use anhydrous ethanol for immersion and washing again, and after sonicating for 5 minutes, discharge the liquid;

13. Introduce dry $N_2$ gas to dry the obtained product, that is, the obtained oxidized cellulose sponge material; and 14. Obtain the completely dried products, that is, the absorbable oxidized cellulose hemostatic product with high porosity and absorptive amount.

The carbonyl content of the prepared oxidized cellulose hemostatic product (hemostatic sponges) is 15% and the porosity thereof is more than 90%.

In the end, it is to be noted that what is illustrated is only the embodiments of the invention. Apparently, the invention is not limited to the embodiments but can include more variations. Any variation directly inferred from or associated with the disclosures of the invention by those of ordinary skill in the art should be considered within the protection scope of the invention.

What is claimed is:

1. A method for preparing an oxidized cellulose hemostatic product, comprising the following steps:
    1) using a sodium hydroxide solution with the concentration of 1 to 5% to pre-process a cellulose product, and after removing lignins or impurities on the fiber surface, using the sodium hydroxide solution to activate the fiber surface further;
    2) after the activating treatment, using demin-water for washing until neutral and drying the obtained cellulose products in air to obtain a raw material;
    3) using a sodium hydroxide solution with the concentration of 5 to 20% as a solvent, adding the cellulose product, carbamide and ZnO that are 3 to 10%, 2% and 2% of the sodium hydroxide solution respectively, and intensively dissolving them under the temperature of −15 to 5° C. to obtain a viscose system;
    4) after the fibers thoroughly dissolve in the solution with a viscose form, adding slowly sodium sulfate as a pore-forming agent and stirring continuously for 20 minutes to make it into a cellulose mixture;
    5) pouring the cellulose mixture into a mould to gelate; during standing, the cellulose solution becoming gelatinous due to the increasing of the viscosity and the loss of mobility, and aging the product for 3 to 24 hours under the condition of −20° C. and −12° C.;
    6) after forming the cellulose gelatin, immerse cellulose gelatin firstly in a coagulating bath under 50 to 70° C., retexturing it for 1 to 3 hours, using demin-water finally for washing until it is neutral, and discharging the wash water to obtain a raw material of the cellulose sponge product;

7) adding an anhydrous ethanol solvent until the raw material of the cellulose sponge product is completely immersed, and after repeated washing, discharging the liquid;

8) performing vacuum drying, and obtaining the preprocessed material of the cellulose sponge after fully drying;

9) adding anhydrous cyclohexane or methyl cyclohexane into an oxidation reactor, adding the preprocessed material of the cellulose sponge, strictly controlling the water content of the system to be less than 0.3%, ensuring that the material of the cellulose sponge is completely immersed in the solution, opening the vacuum to empty the remaining air in the system, and reserving for further use;

10) introducing $NO_2$ gas into the reaction system, and making the concentration of the $NO_2$ gas to be 0.2-4.0 mol/L in the oxidation reaction system; sealing the reaction system and the oxidation reaction of the cellulose sponge material starting at room temperature;

11) after 10-to-40-hour reaction, discharging the oxidation reaction solution into a storage tank;

12) after the reaction, adding the cyclohexane or methyl cyclohexane firstly for washing, and after sonicating for 5 minutes, discharging the liquid; using an ethanol water solution with the mass percent of 50 to 95% for immersion and washing, and after sonicating for 5 minutes, discharging the liquid; when the pH of the effluent is equal to 5 to 7 after repeated washing, using anhydrous ethanol for immersion and washing again, and after sonicating for 5 minutes, discharging the liquid;

13) introducing dry $N_2$ gas to dry the obtained oxidized regenerated cellulose; and 14) obtaining completely dried absorbable oxidized cellulose hemostatic product with high porosity and absorptivity.

2. The method according to claim 1, wherein the cellulose product is cotton fibers, wood fibers or viscoses with the fiber fineness of 0.5 to 3.0 deniers.

3. The method according to claim 1, wherein the coagulating bath contains sodium sulfate and sulfuric acid both with the concentration of 3 to 5% in step 6).

4. The method according to claim 1, wherein air drying at room temperature is adopted to replace vacuum drying in step 8).

5. The method according to claim 1, wherein vacuum freeze drying is adopted to replace drying with $N_2$ gas in step 13).

6. The method according to claim 1, wherein the carboxyl content of the prepared oxidized cellulose hemostatic product is between 15 and 24% and the porosity thereof is more than 90%.

7. The method according to claim 2, wherein the coagulating bath contains sodium sulfate and sulfuric acid both with the concentration of 3 to 5% in step 6).

8. The method according to claim 2, wherein air drying at room temperature is adopted to replace vacuum drying in step 8).

9. The method according to claim 2, wherein the carboxyl content of the prepared oxidized cellulose hemostatic product is between 15 and 24% and the porosity thereof is more than 90%.

10. The method according to claim 5, wherein the carboxyl content of the prepared oxidized cellulose hemostatic product is between 15 and 24% and the porosity thereof is more than 90%.

* * * * *